US011891664B2

(12) United States Patent
Hurley et al.

(10) Patent No.: US 11,891,664 B2
(45) Date of Patent: Feb. 6, 2024

(54) METHODS OF DETECTING RENAL TRANSPLANT REJECTION USING MICROVESICLE NUCLEIC ACID BIOMARKERS

(71) Applicants: Exosome Diagnostics, Inc., Waltham, MA (US); The Brigham and Women's Hospital, Boston, MA (US)

(72) Inventors: James Hurley, Marblehead, MA (US); Christine Coticchia, Waltham, MA (US); Robert Kitchen, Somerville, MA (US); Vasisht Tadigotla, Newton, MA (US); Johan Karl Olov Skog, Lincoln, MA (US); Jamil Azzi, Boston, MA (US)

(73) Assignees: Exosome Diagnostics, Inc., Waltham, MA (US); The Brigham and Women's Hospital, Boston, MA (US)

( * ) Notice: Subject to any disclaimer, the term of this patent is extended or adjusted under 35 U.S.C. 154(b) by 887 days.

(21) Appl. No.: 16/613,298

(22) PCT Filed: May 16, 2018

(86) PCT No.: PCT/US2018/032888
§ 371 (c)(1),
(2) Date: Nov. 13, 2019

(87) PCT Pub. No.: WO2018/213392
PCT Pub. Date: Nov. 22, 2018

(65) Prior Publication Data
US 2020/0199675 A1 Jun. 25, 2020

Related U.S. Application Data

(60) Provisional application No. 62/507,433, filed on May 17, 2017.

(51) Int. Cl.
*C12Q 1/6883* (2018.01)
*G01N 1/28* (2006.01)
*G01N 33/68* (2006.01)

(52) U.S. Cl.
CPC ..... *C12Q 1/6883* (2013.01); *C12Q 2600/158* (2013.01); *G01N 1/28* (2013.01); *G01N 33/6893* (2013.01); *G01N 2800/245* (2013.01); *G01N 2800/347* (2013.01)

(58) Field of Classification Search
None
See application file for complete search history.

(56) References Cited

U.S. PATENT DOCUMENTS

| | | |
|---|---|---|
| 5,639,606 A | 6/1997 | Willey |
| 6,812,023 B1 | 11/2004 | Lamparski et al. |
| 6,899,863 B1 | 5/2005 | Dhellin et al. |
| 7,198,923 B1 | 4/2007 | Abrignani et al. |
| 9,746,479 B2 | 8/2017 | Suthanthiran et al. |
| 9,758,828 B2 | 9/2017 | Suthanthiran et al. |
| 10,472,679 B2 | 11/2019 | Suthanthiran et al. |
| 11,214,833 B2 | 1/2022 | Skog et al. |
| 2015/0353920 A1 | 12/2015 | Enderle et al. |
| 2016/0237422 A1 | 8/2016 | Comper et al. |
| 2016/0348095 A1 | 12/2016 | Russo et al. |
| 2017/0088898 A1 | 3/2017 | Skog et al. |
| 2019/0144941 A1 | 5/2019 | Skog et al. |
| 2019/0284548 A1 | 9/2019 | Stoll et al. |
| 2022/0112555 A1 | 4/2022 | Skog et al. |
| 2023/0203587 A1 | 6/2023 | Skog et al. |

FOREIGN PATENT DOCUMENTS

| | | |
|---|---|---|
| WO | WO-2009100029 A1 | 8/2009 |
| WO | WO 2011/156763 A1 | 12/2011 |
| WO | WO 2014/107571 A1 | 7/2014 |
| WO | WO 2015/021158 A1 | 2/2015 |
| WO | WO 2016/007755 A1 | 1/2016 |
| WO | WO 2016/011383 A1 | 1/2016 |
| WO | WO 2016/054252 A1 | 4/2016 |
| WO | WO 2016/177791 A1 | 11/2016 |
| WO | WO 2017/040515 A1 | 3/2017 |
| WO | WO 2017/192945 A1 | 11/2017 |
| WO | WO 2018/213392 A1 | 11/2018 |
| WO | WO-2021243206 A1 | 12/2021 |

OTHER PUBLICATIONS

Afaneh et al., "Urinary Cell Levels of mRNA for OX40, OX40L, PD-1, PD-L1, or PD-L2 and Acute Rejection of Human Renal Allografts," Transplantation, 90:1381-1387 (2010).
Akalin et al., "Gene expression analysis in human renal allograft biopsy samples using high-density oligoarray technology," Transplantation, 72(5):948-953 (2001).
Bloom et al., "Cell-Free DNA and Active Rejection in Kidney Allografts," J Am Soc Nephrol, 28:2221-2232 (2017). doi: https://doi.org/10.1681/ASN.2016091034.
Chen et al., "Differentially Expressed RNA from Public Microarray Data Identifies Serum Protein Biomarkers for Cross-Organ Transplant Rejection and Other Conditions," PLoS Comput Biol 6(9):e1000940 (2010), 12 pages, doi:10.1371/journal.pcbi.100940.
Cheung et al., "Natural variation in human gene expression in lymphoblastoid cells," Nature Genetics, 33:422-425 (2003).
Christakoudi et al., "Development of a multivariable gene-expression signature targeting T-cell-mediated rejection in peripheral blood of kidney transplant recipients validated in cross-sectional and longitudinal samples," EBioMedicine, 31:571-583 (2019).

(Continued)

*Primary Examiner* — Carla J Myers
(74) *Attorney, Agent, or Firm* — COOLEY LLP; Ivor R. Elrifi; Matthew Pavao

(57) ABSTRACT

The invention relates generally to the use of microvesicle biomarkers such as nucleic acids, including nucleic acid signatures, and/or proteins for assessing a kidney transplant rejection in a patient. The invention further relates to assessing, and/or to monitoring kidney transplant rejection in patients who have received a renal transplant.

8 Claims, 6 Drawing Sheets

(56) References Cited

OTHER PUBLICATIONS

Colvin, "Antibody-Mediated Renal Allograft Rejection: Diagnosis and Pathogenesis," J Am Soc Nephrol, 18:1046-1056 (2007). doi: 10.1681/ASN.2007010073.
Delong, E. R. et al., "Comparing the Areas Under Two or More Correlated Receiver Operating Characteristic Curves: A Nonparametric Approach," Biometrics, 44:837-845 (1988).
Fekih, R. E. et al., "Discovery and Validation of a Urinary Exosome mRNA Signature for the Diagnosis of Human Kidney Transplant Rejection," Journal of the American Society of Nephrology, 32(4):994-1004 (2021).
Gielis et al., "Cell-Free DNA: An Upcoming Biomarker in Transplantation," American Journal of Transplantation, 15:2541-2551 (2015).
Gonzales et al., "Large-Scale Proteomics and Phosphoproteomics of Urinary Exosomes," J Am Soc Nephrol, 20:363-379 (2009), with Supplementary Table 1, 58 pages, doi: 10.1681/ASN.2008040406.
Grimm et al., "Clinical Rejection is Distinguished from Subclinical Rejection by Increased Infiltration by a Population of Activated Macrophages," J Am Spc Nephrol, 10:1582-1589 (1999).
Halloran, P. F. et al., "Antibody-mediated rejection, T cell-mediated rejection, and the injury-repair response: new insights from the Genome Canada studies of kidney transplant bioposies," International, 85:258-264 (2014).
Jung et al., "Potential urinary extracellular vesicle protein biomarkers of chronic active antibody mediated rejection in kidney transplant recipients," Journal of Chromatography B, vol. 1138, Dec. 2020.
Hoshikawa, Y. et al., "Hypoxia induces different genes in the lungs of rats compared with mice," Physiol. Genomics, 12:209-219 (2003).
Hricik et al., "Multicenter Validation of Urinary CXCL9 as a Risk-Stratifying Biomarker for Kidney Transplant Injury," American Journal of Transplantaton, 3:2634-2644 (2013).
Huang et al., "Early clinical experience using donor-derived cell-free DNA to detect rejection in kidney transplant recipients," Am J Transplant, 19:1663-1670 (2019).
Levey, A. S. et al., "Expressing the Modification of Diet in Renal Disease Study Equation for Estimating Glomerular Filtration Rate with Standardized Serum Creatinine Values," Clinical Chemistry, 53(4):766-772 (2007).
Li et al., "Anaylsis of the RNA content of the exosomes derived from blood serum and urine and its potentialas biomarkers," Phil. Trans. R. Soc. B, 396:20130502, 8 pages; http://dx.doi.org/10.1098/rstb.2013.0502.
Lim et al., "Novel urinary exosomal biomarkers of acute T cell-mediated rejection in kidney transplant recipients: A cross-sectional study," PLoS ONE, 13(9):e0204204, 17 pages. https://doi.org/10.1371/journal.pone.0204204.
Manfro et al., "Noninvasive Tim-3 Messenger RNA Evaluation in Renal Transplant Recipients With Graft Dysfunction," Transplantation, 86:1869-1874 (2008).
Martínez-Fernández et al., "RNA Detection in Urine From RNA Extraction to Good Normalizer Molecules," The Journal of Molecular Diagnostics, 18(1):15-22 (2016).
Muthukumar et al., "Messenger RNA for FOXP3 in the Urine of Renal-Allograft Recipients," N Engl J Med, 353:2342-51 (2005).
Orandi et al., "Quantifying Renal Allograft Loss Following Early Antibody-Mediated Rejection," American Journal of Transplantation, 15:489-498 (2015).
Park et al., "Inegrated Kidney Exosome Analysis for the Detection of Kidney Transplant Rejection," ACS Nano, 11:11041-11046 (2017).
Pisitkun et al., "Identification and proteomic profiling of exosomes in human urine," PNAS, 101(36):13368-13373 (2004).
Sigdel et al., "Optimizing Detection of Kidney Transplant Injury by Assessment of Donor-Derived Cell-Free DNA via Massively Multiplex PCR," J. Clin. Med., 8(19) (2019), 17 pages. doi:10.3390/jcm8010019.
Spivey et al., "Gene expression profiling in acute allograft rejection: challenging the immunologic constant of rejection hypothesis," Journal of Translational Medicine, 9(174) (2011), 22 pages. http://www.translational-medicine.com/content/9/1/174.
Sreekumar et al., "Differential Allograft Gene Expressing in Acute Cellular Rejection and Recurrence of Hepatitis C After Liver Transplantation," Liver Transpl, 8:814-821.
Suthanthiran et al., "Urinary-Cell mRNA Profile and Acute Cellular Rejection in Kidney Allografts," N Engl J Med, 369:20-31 (2013). doi:10.1056/NEJMoa1215555.
Wu et al., "Single-Cell Transcriptomics of a Human Kidney Allograft Biopsy Specimen Defines a Diverse Inflammatory Response," J Am Soc Nephrol, 29:2069-2080 (2018), and Supplementary Information, 15 pages. doi: https://doi.org/10.1681/ASN.2018020125.
Yang et al., "A urine score for noninvasive accurate diagnosis and prediction of kidney transplant rejection," Sci. Transl. Med., 12:eaba2501 (2020), 11 pages.
Zhang et al., "Plasma Exosomes From HLA-Sensitized Kidney Transplant Recipients Contain mRNA Transcripts Which Predict Development of Antibody-Mediated Rejection," Transplantation, 101(10):2419-2428 (2017).
Al-Nedawi et al., "Intracellular transfer of the oncogenic receptor EGFRvIII by microvesicles derived from tumour cells." Nat Cell Biol. (2008); 10(5): 619-624.
Alvarez et al., "Urinary exosomes as a source of kidney dysfunction biomarker in renal transplantation." Transplant Proc. (2013); 45(10): 3719-3723.
Assaker et al., "Discovery and Validation of a Urinary Exosome mRNA Signature for the Diagnosis of Human Kidney Transplant Rejection." Abstract#494, American Journal of Transplantation, American Transplant Congress, ATC 2018, vol. 18, Supplement 4, pp. 436-437.
Balzar et al., "The biology of the 17-1A antigen (Ep-CAM)." J Mol Med. (1999); 77(10): 699-712.
Brock et al. "Liquid Biopsy for cancer screening, patient stratification and monitoring." Translational Cancer Center Research, (2015); 4(3): 280-290.
Chen et al., "Microfluidic isolation and transcriptome analysis of serum microvesicles." Lab Chip (2010); 10(4): 505-511.
Cheruvanky, et al., "Rapid isolation of urinary exosomal biomarkers using a nanomembrane ultrafiltration concentrator." Am J Physiol Renal Physiol. (2007); 292: F1657-F1661.
Enderle et al., "Characterization of RNA from Exosomes and other Extracellular Vesicles Isolated by a Novel Spin Column-Based Method." PLoS One (2015); 10(8): e0136133, pp. 1-19.
Harada et al., "Non-Invasive Diagnosis of Post Kidney Transplant Complications by Urinary Exosomal mRNA Analysis." Meeting Abstracts, Abstract No. 182 (May 4, 2015). Retrieved on Feb. 1, 2019, 15(7): 477-484, 5 pages.
Hahn, "Molecular biology of double-minute chromosomes." BioEssays (1993); 15(7): 477-484.
Jackson et al., "Urinary Chemokines CXCL9 and CXCL10 Are Noninvasive Markers of Renal Allograft Rejection and BK Viral Infection." American Journal of Transplantation (2011); 11: 2228-2234.
Miranda et al., "Nucleic acids within urinary exosomes/microvesicles are potential biomarkers for renal disease." Kidney International (2010); 78(2): 191-199.
Murakami et al., "Development of glomerulus-, tuble-, and collecting duct—specific mRNA assay in human urinary exosomes and microvesicles." PLoS ONE (2014); 9(9): 10 pages.
Nilsson et al., "Prostate cancer-derived urines exosomes: a novel approach to biomarkers for prostate cancer." British Journal of Cancer (2009); 100: 1603-1607.
Raposo et al., "B lymphocytes secrete antigen-presenting vesicles." Journal of Experimental Medicine (1996); 183: 1161-1172.
Sigdel et al., "Perturbations in the urinary exosome in transplant rejection." Front Med (Lausanne) (2014); 1:57; Published online Jan. 5, 2015, 10 pages; doi: 10.3389/fmed.2014.00057.
Skog et al., "Glioblastoma microvesicles transport RNA and proteins that promote tumour growth and provide diagnostic biomarkers." Nature Cell Biology (2008); 10(12): 1470-1476.
Tatapudi et al., "Noninvasive detection of renal allograft inflammation by measurements of mRNA for IP-10 and CXCR3 in urine." Kidney International (2004); 65: 2390-2397.

(56) References Cited

OTHER PUBLICATIONS

Taylor and Gercel-Taylor, "MicroRNA signatures of tumor-derived exosomes as diagnostic biomarkers of ovarian cancer." Gynecol Oncol. (2008); 110: 13-21.
Went et al., "Frequent epcam protein expression in human carcinomas." Hum Pathol. (2004); 35:122-128.
Zhang et al., "mRNA Transcript Profiles of 14 Genes in Plasma Exosome Predict Risk for Antibody-Mediated Rejection (ABMR) of Renal Allografts." Abstract #23, American Journal of Transplantation, American Transplant Congress, ATC 2018, vol. 18, Supplement 4, 1 page.
Applied Biosystems by Life Technologies, User Guide, TaqMan OpenArray Pathway Panels, Nov. 5, 2016, printed from assets.fishersci.com, 2013, 26 pages.
Coticchia, et al., "Urine Exosome Proteins CXCL9 ands CXCL10 are Predictors of Kidney Transplant Rejections," Journal of Extracellular Vesicles, May 15, 2017, p. 207.
Kursa, et al., "Feature selection with the Boruta package," Journal of statistical software, Sep. 2010, 13 pages.
Meehan, et al., "The relationship of untreated borderline infiltrates by the Banff criteria to acute rejection in renal allograft biopsies," Journal of the American Society of Nephrology, Aug. 1999, pp. 1806-1814.

METHODS OF DETECTING RENAL TRANSPLANT REJECTION USING MICROVESICLE NUCLEIC ACID BIOMARKERS

RELATED APPLICATIONS

This application is a U.S. National Phase Application, filed under 35 U.S.C. 371, of International Application No. PCT/US2018/032888, filed on May 16, 2018. International Application No. PCT/US2018/032888 claims priority to, and the benefit of U.S. Provisional Application No. 62/507,433, filed May 17, 2017. The contents of each of the aforementioned patent applications are incorporated herein by reference in their entireties.

FIELD OF THE INVENTION

The invention relates generally to the use of microvesicle biomarkers such as nucleic acids, including nucleic acid signatures, and/or proteins for assessing a kidney transplant rejection in a patient. The invention further relates to assessing, and/or to monitoring kidney transplant rejection in patients who have received a renal transplant.

BACKGROUND

Increasing knowledge of the genetic and epigenetic changes occurring in cells provides an opportunity to detect, characterize, and monitor diseases and disorders by analyzing disease-specific nucleic acid and protein sequences and profiles. These changes can be observed by detecting any of a variety of disease-related biomarkers. Various molecular diagnostic assays are used to detect these biomarkers and produce valuable information for patients, doctors, clinicians and researchers.

The ability to perform these tests using a bodily fluid sample has wide ranging implications in terms of patient welfare, the ability to conduct longitudinal disease monitoring, and the ability to obtain expression profiles even when tissue cells are not easily accessible.

Accordingly, there exists a need for new, noninvasive methods of detecting biomarkers, for example, biomarkers in microvesicles, to aid in the characterization, diagnosis, monitoring, or therapy selection for a disease or other medical condition.

SUMMARY OF THE INVENTION

In one aspect, the invention relates to a method for assessing a kidney rejection in a patient, the method comprising the steps of:
a) isolating a microvesicle fraction from a patient's biological sample;
b) extracting a plurality of biomarkers from the microvesicle fraction;
c) determining the expression levels of at least one biomarker from the plurality of biomarkers in the patient sample;
d) optionally normalizing the expression level of at least one biomarker; and,
e) measuring the expression level of at least one biomarker to determine whether the patient is undergoing a kidney rejection vs. non-rejection.

In one preferred embodiment, the kidney rejection is a kidney transplant rejection.

In some embodiments, the plurality of biomarkers identified by any one of the methods disclosed herein comprise RNA, while in other embodiments, the plurality of biomarkers comprise protein. In some embodiments, the plurality of biomarkers comprise a combination of RNA and protein.

In one embodiment, a subject herein is a patient who has received a renal transplant. In some embodiments, assessing a kidney rejection in a subject provides a prognostic factor for the patient.

In a related aspect, the invention relates to methods of using microvesicle RNA signatures to assess, assay, determine, measure, characterize, identify or diagnose, a kidney transplant rejection in a subject, where in some embodiments the subject is a human adult. In other embodiments, the subject is a human child. In some embodiments, the methods are used to monitor treatment efficacy longitudinally.

The methods and compositions provided herein are useful for measuring nucleic acids obtained from microvesicles, e.g., microvesicle RNA, also referred to herein as exosome RNA or exosomal RNA, and proteins obtained from microvesicles, e.g., microvesicle or exosome protein, as a diagnostic for transplant rejection such as, for example, kidney transplant rejection.

Traditionally, biomarker discovery and development has required the use of material obtained from tissue biopsies. However, recent developments in the microvesicle field have allowed biomarker research in biofluids to evolve. Exosomes are highly stable microvesicles, approximately 30-200 nm in diameter, that are shed by cells into all biofluids, including blood, urine, and cerebrospinal fluid, carrying a rich source of intact protein and RNA. Exosomes and other vesicles can be released by multi-vesicular body pathway or through direct budding at the plasma membrane. RNA can be efficiently isolated and addressed using technologies such as RT-qPCR and NGS (see e.g., Brock, G. et al. (2015) Liquid biopsy for cancer screening, patient stratification and monitoring. Translational Cancer Research, 4(3), 280-290; and Enderle, D. et al. (2015) Characterization of RNA from Exosomes and Other Extracellular Vesicles Isolated by a Novel Spin Column-Based Method. PLoS ONE, 10(8): e0136133. doi:10.1371/journal.pone.0136133).

In some embodiments, the methods and kits described herein isolate the microvesicle fraction by capturing the microvesicles to a surface and subsequently lysing the microvesicles to release the nucleic acids, particularly RNA or protein contained therein. The methods and kits provided herein isolate the microvesicle fraction using any suitable technique. In some embodiments, the microvesicles are isolated using the methods and capture surfaces described in PCT Publication No. WO 2014/107571 and in PCT Publication No. WO 2016/007755, the contents of each of which are hereby incorporated by reference in their entirety. In some embodiments, the microvesicles are isolated from a urine sample using the methods and capture surfaces described in PCT Publication No. WO 2015/021158, the contents of which are hereby incorporated by reference in their entirety. In some embodiments, the microvesicles are isolated from a urine sample by using immunocapture method. In some embodiments, the immune capture surface is a column. In some embodiments, the immune capture surface is a bead or any other solid surface.

In one aspect, the invention relates to methods of detecting a plurality of biomarkers in a biological sample to aid in diagnosis, monitoring, or therapy selection for transplant rejection such as, for example, kidney transplant rejection. The methods and kits provided herein are useful in detecting a plurality of biomarkers from the microvesicle fraction of a patient's biological sample, e.g., a urine sample.

In one aspect, the optional normalizing step comprises comparing the expression levels of at least one of the biomarkers with at least one normalizing gene or at least one normalizing protein.

In another aspect, the set of biomarkers comprises a gene signature. In another aspect, at least one biomarker comprise a gene signature. In some embodiments, the gene signature comprise at least one of the genes CXCL9, CXCL10, and IL17RA. In some embodiments, at least one biomarker or at least one normalizing gene comprise a gene signature having at least one of the genes CXCL9, CXCL10, and IL17RA.

In another aspect, the plurality of biomarkers comprise protein. In another embodiment, the set of biomarkers comprise a protein signature. In some embodiments, proteins encompass the multitude of protein forms including proteins, protein monomers, protein complexes and protein aggregates. In some embodiments, at least one biomarker or normalizing protein comprise at least one protein biomarker selected from Table 4. In other embodiments, at least one biomarker or at least one normalizing protein comprise at least one of MCP-4, MCP-1, CX3CL1, CXCL9, CXCL10, CCL11, PD-L1, ADA, IL-8, and CSF-1 or a combination thereof.

In another aspect, the method disclosed herein is performed on a periodic basis to monitor the progress of kidney transplant rejection in a patient. In another embodiment, the patient is undergoing a kidney rejection therapy.

In one embodiment, the method disclosed herein comprises selecting a therapy for kidney transplant rejection, monitoring a therapy for kidney transplant rejection or optimizing an ongoing kidney transplant rejection therapy.

Various aspects and embodiments of the invention will now be described in detail. It will be appreciated that modification of the details may be made without departing from the scope of the invention. Further, unless otherwise required by context, singular terms shall include pluralities and plural terms shall include the singular.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

BRIEF DESCRIPTION OF THE FIGURES

The above and further features will be more clearly appreciated from the following detailed description when taken in conjunction with the accompanying drawings.

FIG. 5 shows a box plot of eight proteins (from the 92 examined) that are differentially expressed between non-rejection and rejection samples, P=0.05, ANOVA).

FIG. 6 shows a box plot of three highly significant exosome proteins that are differentially expressed between non-rejection and rejection samples, P=0.01, ANOVA).

DETAILED DESCRIPTION OF THE INVENTION

Figure 1:
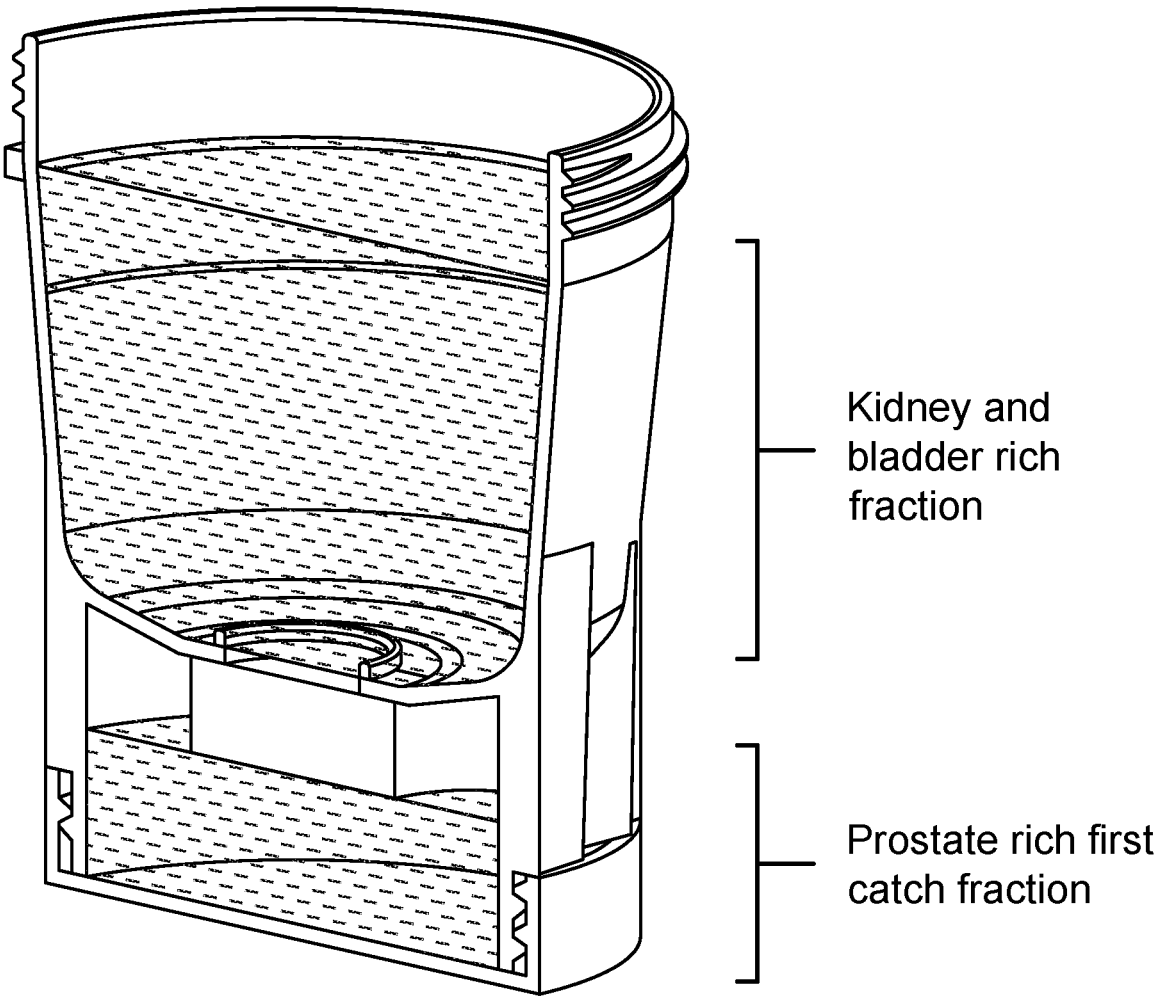
FIG. 1 illustrates a modified urine collection cup diagram (see WO2016/054252, which is incorporated by reference herein in its entirety)—which is a urine collection device for generation of a fractional urine sample. The cup is optimized for first or midstream urine collection. Prostate rich extracellular vesicles (EVs) found in the first urine catch are captured in the bottom of the cup, while urine with EVs from kidney and bladder are collected in the upper chamber of the cup.

The disclosure provides methods for the use of nucleic acids and protein biomarkers isolated from microvesicles to assess a kidney rejection and/or to monitor kidney rejection treatment efficacy. In some embodiments, the methods are used to monitor treatment efficacy longitudinally.

In some embodiments, the biomarkers are differentially expressed in a patient with kidney rejection vs non-rejection.

In one particular embodiment, provided is a method for assessing a kidney rejection in a patient, the method comprising the steps of:
  a) isolating a microvesicle fraction from a patient's biological sample;
  b) extracting a plurality of biomarkers from the microvesicle fraction;
  c) determining the expression levels of at least one biomarker from the plurality of biomarkers in the patient sample;
  d) optionally normalizing the expression level of at least one biomarker; and, e) measuring the expression level of at least one biomarker to determine whether the patient is undergoing a kidney rejection vs. non-rejection.

In one particular embodiment, provided is a method for assaying a kidney rejection in a patient, the method comprising the steps of:
a) isolating a microvesicle fraction from a patient's biological sample;
b) extracting a plurality of biomarkers from the microvesicle fraction;
c) assaying the expression levels of at least one biomarker from the plurality of biomarkers in the patient sample;
d) optionally normalizing the expression level of at least one biomarker; and,
e) assaying the expression level of at least one biomarker to determine whether the patient is undergoing a kidney rejection vs. non-rejection.

In another embodiment, the method comprises assaying, assessing, determining, measuring, characterizing, identifying or diagnosing a kidney rejection in a patient. In another embodiment, the kidney rejection is a kidney transplant rejection.

In one embodiment, the optionally normalizing step disclosed herein comprises comparing the level of expression of at least one biomarker with an expression profile of a set of control biomarkers. In one embodiment, the set of control biomarkers comprises one or more normalizing gene(s). In another embodiment, the set of control biomarkers comprise one or more normalizing protein(s). In another embodiment, at least one biomarker is differentially expressed as compared to the expression profile of the control set of biomarkers representing a patient having a kidney rejection. In another embodiment, at least one biomarker is differentially expressed as compared to the expression profile of the control set of biomarkers representing a patient without a kidney rejection.

In one embodiment, the optional normalizing step comprises comparing the expression levels of at least one of the biomarkers with a known biomarker signature. In another embodiment, the optional normalizing step comprises comparing the expression levels of at least one of the biomarkers with a control biomarker signature. In another embodiment, the optional normalizing step comprises comparing the expression levels of at least one of the biomarkers with a control biomarker gene signature. In another embodiment, the optional normalizing step comprises comparing the expression levels of at least one of the biomarkers with a control biomarker protein signature.

In one embodiment, the optional normalizing step comprises comparing the expression levels of at least one of the biomarkers with the expression profile of a normalized gene or genes. In another embodiment, the optional normalizing step herein comprises comparing the expression levels of at least one of the biomarkers with the expression profile a control biomarker gene signature. In one embodiment, the gene signature comprises at least one of the genes CXCL9, CXCL10, and IL17RA. In one embodiment, a normalizing gene comprises a gene selected from CXCL9, CXCL10, IL17RA or a combination thereof.

In one embodiment, the normalizing step comprises determining a normalized, relative expression level of the biomarker, wherein the relative expression level of the biomarker is a ratio between the level of biomarker expression to the level of reference gene expression, wherein the subject is identified as suffering from a kidney rejection, or having a medical condition of the kidney leading to rejection when the relative expression level of the biomarker is greater than a cutoff level of biomarker expression. In some embodiments, the relative expression level of the biomarker is lower than a cutoff level of biomarker expression. In some embodiments, the medical condition of the kidney comprises a kidney or kidney transplant rejection of any type known in the art and of any type as further disclosed herein.

In one embodiment, the cutoff level of biomarker expression is a score based on a collective level of biomarker expression in a control group of subjects that are suffering from a kidney rejection or medical condition leading to a kidney rejection. In other embodiments, the kidney rejection is a kidney transplant rejection. Such a score may help identify a patient as being free of rejection vs non-rejection.

In some embodiments, the cutoff level of biomarker expression is a score based on a collective level of biomarker expression in a control group of subjects that are suffering from any type of kidney rejection, including, but not limited to, cellular rejection including borderline rejection, antibody mediated rejection (AMR) either acute or chronic active, or cellular and AMR, clinical rejection, or a combination thereof.

In other embodiments, the cutoff level of biomarker expression is a score based on a collective level of biomarker expression in a control group of subjects that are not suffering from a kidney rejection. Such a score may help determine or characterize a patient as having a kidney rejection. Hence, when using the methods disclosed herein a skilled artisan is able to characterize a patient as either having or not having a kidney rejection.

In some embodiments, the cutoff level of biomarker expression is a score based on a collective level of biomarker expression in a control group of subjects that are not suffering from a kidney transplant rejection.

In some embodiments, the cutoff level of biomarker expression is a score based on a collective level of biomarker expression in a control group of subjects that are not suffering from any type of kidney rejection, including, but not limited to, cellular rejection including borderline rejection, antibody mediated rejection (AMR) either acute or chronic active, or cellular and AMR, clinical rejection, or a combination thereof.

In one embodiment, the plurality of biomarkers comprise at least one RNA. In some embodiments, the methods and compositions provided herein are useful for measuring nucleic acids obtained from microvesicles, e.g., microvesicle RNA, also referred to herein as exosome RNA or exosomal RNA, as a diagnostic for transplant rejection such as, for example, kidney transplant rejection.

Microvesicles are shed by eukaryotic cells, or budded off of the plasma membrane, to the exterior of the cell. These membrane vesicles are heterogeneous in size with diameters ranging from about 10 nm to about 5000 nm. All membrane vesicles shed by cells <0.8 µm in diameter are referred to herein collectively as "extracellular vesicles" or "microvesicles." These extracellular vesicles include microvesicles, exosomes, microvesicle-like particles, prostasomes, dexosomes, texosomes, ectosomes, oncosomes, apoptotic bodies, retrovirus-like particles, and human endogenous retrovirus (HERV) particles. Small microvesicles (approximately 10 to 1000 nm, and more often 30 to 200 nm in diameter) that are released by exocytosis of intracellular multivesicular bodies are referred to in the art as "microvesicles."

In some embodiments, the terms "exosomes", "microvesicles" and extracellular vesicles (EVs) are used interchangeably herein. In some embodiments, the methods disclosed herein comprise isolating a microvesicle fraction from a patient's biological sample.

In one embodiment, the set of control biomarkers comprise at least one RNA. In another embodiment, the set of control biomarkers comprise a gene signature.

In one embodiment, when the plurality of biomarkers comprises RNA, the method in step d) herein comprises comparing the expression levels of at least one of the RNA biomarkers from the plurality of biomarkers with a known or control set of RNA biomarkers.

In another embodiment, one or more known or control RNA biomarker comprise CXCL9, CXCL10, IL17RA or a combination thereof. In another embodiment, one or more known or control RNA biomarker is selected from the list consisting of CXCL9, CXCL10, and IL17RA. In another embodiment, at least one normalizing gene comprises CXCL9, CXCL10, IL17RA or a combination thereof. In another embodiment, at least one normalizing gene is selected from the list consisting of CXCL9, CXCL10, and IL17RA.

In one embodiment, at least one biomarker or at least one normalizing gene comprise a gene signature having at least one of the genes CXCL9, CXCL10, and IL17RA.

As will be understood by a skilled artisan, the term "nucleic acids" refer to DNA and RNA. The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements. In any of the methods disclosed herein, the nucleic acids are DNA or RNA. Examples of RNA include messenger RNAs, transfer RNAs, ribosomal RNAs, small RNAs (non-protein-coding RNAs, non-messenger RNAs), microRNAs, piRNAs, exRNAs, snRNAs and snoRNAs. In some embodiments, the RNA is miRNA.

In any of the foregoing methods, the nucleic acids are isolated from or otherwise derived from a microvesicle fraction. In some embodiments, the nucleic acids are RNA or DNA or RNA and DNA isolated from or otherwise derived from a microvesicle fraction. In some embodiments, the nucleic acids are RNA isolated from or otherwise derived from a microvesicle fraction.

In any of the methods disclosed herein, the nucleic acids are cell-free nucleic acids, also referred to herein as circulating nucleic acids. In some embodiments, the cell-free nucleic acids are DNA or RNA. In some embodiments, the cell-free nucleic acid is cell-free DNA. In some embodiments the cell-free nucleic acids is DNA and RNA.

In one embodiment, the plurality of biomarkers comprise at least one protein.

In another embodiment, the set of control biomarkers comprise at least one protein biomarker. In another embodiment, the set of control biomarkers comprise a protein signature. In another embodiment, when the plurality of biomarkers comprises protein, the optional normalizing step comprises comparing the expression levels of at least one of the protein biomarkers from the plurality of biomarkers with a known or control set of protein biomarkers. In another embodiment, when the plurality of biomarkers comprises protein, the optional normalizing step comprises comparing the expression levels of at least one of the protein biomarkers from the plurality of biomarkers with at least one normalizing protein. In another embodiment, when the plurality of biomarkers comprises protein, the method in step d) comprises comparing the expression levels of at least one of the protein biomarkers from the plurality of biomarkers with at least one protein biomarker from Table 4. In another embodiment, when the plurality of biomarkers comprises proteins, the normalizing step comprises comparing the expression levels of at least one of the protein biomarkers from the plurality of biomarkers with at least one protein biomarkers from the following: MCP-4, MCP-1, CX3CL1, CXCL9, CXCL10, CCL11, PD-L1, ADA, IL-8, and CSF-1 or a combination thereof. In another embodiment, at least one normalizing protein is selected from Table 4.

In one embodiment, a control protein signature is selected from Table 4. In another embodiment, one or more known or control protein biomarker is selected from Table 4. In another embodiment, one or more known or control protein biomarker comprises MCP-4, MCP-1, CX3CL1, CXCL9, CXCL10, CCL11, PD-L1, ADA, IL-8, CSF-1 or a combination thereof. In another embodiment, one or more known or control protein biomarker is selected from the list consisting of MCP-4, MCP-1, CX3CL1, CXCL9, CXCL10, CCL11, PD-L1, ADA, IL-8, and CSF-1. In another embodiment, at least one normalizing protein is selected from the following: MCP-4, MCP-1, CX3CL1, CXCL9, CXCL10, CCL11, PD-L1, ADA, IL-8, and CSF-1 or a combination thereof.

In one embodiment, at least one biomarker(s) and/or at least one normalizing protein comprise at least one protein(s) selected from Table 4. In another embodiment, at least one biomarker and/or at least one normalizing protein comprise at least one of MCP-4, MCP-1, CX3CL1, CXCL9, CXCL10, CCL11, PD-L1, ADA, IL-8, and CSF-1 or a combination thereof.

In one embodiment, the set of biomarkers isolated from a patient's sample is from one or more cohorts/groups of patients who have experienced a kidney transplant rejection as well as from one or more cohorts/groups of patients or cohorts/groups of patients who have not experienced any symptom of kidney rejection. In some embodiments, the cohorts/groups of patients or a cohorts/groups of patients who have not experienced any symptom of kidney rejection have no clinical indications of either cellular or antibody-mediated rejection. In one embodiment, the methods disclosed herein further comprise using an algorithm for identifying a kidney transplant rejection. In another embodiment, the algorithm comprises using at least one of the following risk factors: a) female; b) age <50; c) African American;) repeat transplant; e) current Panel Reactive Antibody (PRA)>25% (some studies showed >0%): it measures the presence of HLA antibodies; 0 number of human leukocyte antigen (HLA) mismatch (A, B and DR): 3-6 mismatch; g) deceased kidney; h) delayed graft function; i) presence of donor specific antibodies; j) no thymoglobulin induction; or a combination thereof.

In one embodiment, the method disclosed herein comprises determining the type of kidney rejection in the patient. In another embodiment, the kidney rejection is a kidney transplant rejection. In another embodiment, the type of kidney rejection is cellular rejection including borderline rejection, antibody mediated rejection (AMR) either acute or chronic active, or cellular and AMR, clinical rejection, or a combination thereof. In another embodiment, the type of kidney transplant rejection disclosed herein comprises cellular rejection including borderline rejection, antibody mediated rejection (AMR) either acute or chronic active, or cellular and AMR, clinical rejection, or a combination thereof.

In one embodiment, a criteria for urine samples from kidney transplant rejection patients includes cellular rejection including borderline rejection, antibody mediated rejection (AMR) either acute or chronic active or cellular and AMR.

In one embodiment, a biological sample is obtained from a patient having kidney rejection or non-rejection. In some embodiments, a microvesicle fraction is isolated from a patient's biological sample. As used herein, the term "biological sample" refers to a sample that contains biological materials such as DNA, RNA and protein.

In some embodiments, the biological sample may suitably comprise a bodily fluid from a subject. The bodily fluids can be fluids isolated from anywhere in the body of the subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

In some embodiments, the biological sample may suitably comprise a tissue sample from a subject. The tissue sample can be isolated from anywhere in the body of the subject.

A suitable sample volume of a bodily fluid is, for example, in the range of about 0.1 ml to about 30 ml fluid. The volume of fluid may depend on a few factors, e.g., the type of fluid used. For example, the volume of serum samples may be about 0.1 ml to about 4 ml, preferably about 0.2 ml to 4 ml. The volume of plasma samples may be about 0.1 ml to about 4 ml, preferably 0.5 ml to 4 ml. The volume of urine samples may be about 10 ml to about 30 ml, preferably about 20 ml.

While the examples provided herein used plasma samples, the skilled artisan will appreciate that these methods are applicable to a variety of biological samples. Other suitable biological samples include urine, cerebrospinal fluid, blood including blood components, e.g., plasma and serum, sputum, pleural fluid, nipple aspirates, lymph fluid, fluid of the respiratory, intestinal, and genitourinary tracts, tear fluid, saliva, breast milk, fluid from the lymphatic system, semen, intraorgan system fluid, ascitic fluid, tumor cyst fluid, amniotic fluid, cell culture supernatant and combinations thereof.

The methods and kits of the disclosure are also suitable for use with samples derived from a human subject. The methods and kits of the disclosure are suitable for use with samples derived from a non-human subject such as, for example, a rodent, a non-human primate, a companion animal (e.g., cat, dog, horse), and/or a farm animal (e.g., chicken).

The term "subject" is intended to include humans and animals shown to or expected to have nucleic acid-containing extracellular vesicles. The term also includes humans and animals show to or expected to have protein-containing extracellular vesicles. In particular embodiments, the subject is a mammal, a human or nonhuman primate, a dog, a cat, a horse, a cow, other farm animals, or a rodent (e.g. mice, rats, guinea pig etc.). A human subject may be a normal human being without observable abnormalities, e.g., a disease. A human subject may be a human being with observable abnormalities, e.g., a disease. A human subject may be a human adult or child. The observable abnormalities may be observed by the human being himself, or by a medical professional. The term "subject," "patient," and "individual" are used interchangeably herein.

In another embodiment, the method of assessing a patient as having a kidney rejection further comprises monitoring a therapy for kidney rejection. In one embodiment, the method provided herein is performed on a periodic basis following an initial assessment, to monitor the progress of kidney rejection in a patient receiving kidney rejection therapy.

In some embodiments, the method is performed every day, every week, bi-weekly, tri-weekly, monthly, every 2 months, ever 2-12 months, every year, or every 2-5 years. In other embodiments, the method disclosed herein can be performed on a need-to basis following an episode of kidney rejection in a patient that has received a kidney transplant. In other embodiments, the method disclosed herein can be performed on a need-to basis following an episode of kidney rejection in a patient following renal failure.

In one embodiment, the method of assessing a patient as having a kidney rejection further comprises selecting a therapy for kidney rejection. In one embodiment, the method of assessing a patient as having a kidney rejection further comprises selecting an optimal therapy for a patient having a kidney rejection, where in some embodiments, a skilled artisan will compare several therapies available in the art, to determine the optimal one for the particular patient in need of the therapy.

In one embodiment, kidney rejection therapy may comprise any type of therapy available in the art, including immunosuppressive therapy, according to current standard guidelines (PMDID: PMC5455080) for kidney transplantation. Current standard guidelines for diagnosis of kidney transplant rejection include core needle biopsy of the kidney followed by immunohistochemical and histological analysis of the tissue sample by a pathologist.

In some embodiments, for a patient undergoing kidney rejection therapy, the method disclosed herein allows selection of the kidney rejection therapy to prevent or reduce progression of a kidney rejection in the patient.

In some embodiments, optimization of a kidney rejection or kidney disease therapy being administered to a patient in need by using the methods disclosed herein further comprises making any necessary therapy adjustments, as will be determined by the clinician, to improve the efficacy of the kidney rejection therapy. These adjustments may include, but are not limited to, drug or drug cocktail adjustments, drug formulation adjustments, drug dose adjustments, drug dose administration schedule adjustments, use of additional medications (e.g. to manage an infection, treat hypertension, etc.) or any combination thereof, including any other treatment modality available in the art.

In some embodiments, a biological sample (e.g., a urine sample, and/or the like) may be collected for analysis, e.g., to determine a person's health and/or the like. In some embodiments, a modified sample collection cup (see FIG. 1) may be configured to separate portions of a sample from other portions of the sample (e.g., a first volume of the sample, and/or the like may be separated from other portions of the sample), in order to obtain optimal results. In some embodiments, parts of the container may be sealed in a plurality of ways in order to prevent leakage or spills, e.g., during transit and/or the like, and to prevent dilution of the portions of the sample. Examples of this sample collection cup are described in WO 2016/054252, which is incorporated by reference herein in its entirety.

For example, a modified sample collection containers may be formed via a bottom-cap design, a two-cup design, and/or the like. Referring to FIG. 1 of WO 2016/054252, in some embodiments, a laboratory may use a bottom-cap design 102 for the sample collection container. In some embodiments, the container may comprise a dual-seal top cap 104, a single molded collection cup 106, a float device 108, and a screw-on bottom cap 110. In some embodiments, the collection container may also have room for a label 112 on which sample identification information (e.g., the name of the patient, the date and time the sample was obtained, the type of sample obtained, and/or the like) may be imprinted.

In some embodiments, a standard urine collection cup is used to collect urine and the like, where in some embodiments, this standard cup is used to collect at least 30 ml of a patient's urine sample.

The methods of the disclosure use at least 30 ml of a second catch urine sample from a subject, e.g., where a sample between 25-40 mL of first catch urine is discarded.

In a preferred embodiment, the urine sample is the urine that follows the first voided from the bladder, which is referred to as "second catch" urine. The second or subsequent to the first voided urine contains the highest concentration of kidney-derived microvesicles, and therefore the analysis of the second or subsequent voided urine provides higher signal from kidney biomarkers.

In one embodiment, a method of increasing a kidney-specific biomarker signal, comprises the steps of a) collecting a patient's biological sample from an upper chamber of a modified urine cup (see FIG. 1) or collecting at least about 30 ml in a standard collection cup; wherein the biological sample is urine; b) isolating a microvesicle fraction from the patient's biological sample containing a plurality of kidney-specific biomarkers; and, c) extracting the plurality of kidney-specific biomarkers from the microvesicle fraction, thereby increasing a kidney-specific biomarker signal.

In another embodiment, the method of increasing a kidney-specific biomarker signal further comprises the steps of: d) determining the expression levels of at least one biomarker from the plurality of biomarkers in the patient sample; e) optionally normalizing the expression level of at least one biomarker; and, f) measuring the expression level of at least one biomarker to determine whether the patient is undergoing a kidney rejection vs. non-rejection.

In another embodiment, the collecting from the upper chamber of the modified cup or collecting at least about 30 ml of urine in a standard urine collection cup increases the concentration of kidney-specific microvesicles. In another embodiment, at least about 30-40 ml, 41-50 ml, 51-60 ml, or 61-70 ml of urine is collected in a standard urine collection cup or equivalent.

In embodiments where the microvesicle isolation method employs a capture surface. In some embodiments, the capture surface is a membrane and the device for isolating the microvesicle fraction from a biological sample contains at least one membrane. In some embodiments, the device comprises one, two, three, four, five or six membranes. In some embodiments, the device comprises three membranes. In embodiments where the device comprises more than one membrane, the membranes are all directly adjacent to one another at one end of the column. In embodiments where the device comprises more than one membrane, the membranes are all identical to each other, i.e., are of the same charge and/or have the same functional group.

It should be noted that microvesicle capture by filtering through a pore size smaller than the microvesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use any of a variety of capture surfaces. In some embodiments, the capture surface is a membrane, also referred to herein as a filter or a membrane filter. In some embodiments, the capture surface is a commercially available membrane. In some embodiments, the capture surface is a charged commercially available membrane. In some embodiments, the capture surface is neutral. In some embodiments, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In one embodiment, when a membrane is used as the capture surface, it should be understood that the format of the capturing surface, e.g., beads or a filter (also referred to herein as a membrane), does not affect the ability of the methods provided herein to efficiently capture microvesicles from a biological sample.

A wide range of surfaces are capable of capturing microvesicles according to the methods provided herein, but not all surfaces will capture microvesicles (some surfaces do not capture anything).

In some embodiments, the capture surface is positively charged. In another embodiment, the capture surface is negatively charged. In yet another embodiment, the capture surface is neutral. In some embodiments, the capture surface is modified with antibodies, peptides, epitopes or ligands for immunocapture methods.

In embodiments where the capture surface is charged, the capture surface can be a charged filter selected from the group consisting of 0.65 μm positively charged Q PES vacuum filtration (Millipore), 3-5 μm positively charged Q RC spin column filtration (Sartorius), 0.8 μm positively charged Q PES homemade spin column filtration (Pall), 0.8 μm positively charged Q PES syringe filtration (Pall), 0.8 μm negatively charged S PES homemade spin column filtration (Pall), 0.8 μm negatively charged S PES syringe filtration (Pall), and 50 nm negatively charged nylon syringe filtration (Sterlitech). Preferably, the charged filter is not housed in a syringe filtration apparatus, as Qiazol/RNA is harder to get out of the filter in these embodiments. Preferably, the charged filter is housed at one end of a column.

In embodiments where the capture surface is a membrane, the membrane can be made from a variety of suitable materials. In some embodiments, the membrane is polyethersulfone (PES) (e.g., from Millipore or PALL Corp.). In some embodiments, the membrane is regenerated cellulose (RC) (e.g., from Sartorius or Pierce).

In some embodiments, the capture surface is a positively charged membrane. In some embodiments, the capture surface is a Q membrane, which is a positively charged membrane and is an anion exchanger with quaternary amines. For example, the Q membrane is functionalized with quaternary ammonium, $R-CH_2-N^+(CH_3)_3$. In some embodiments, the capture surface is a negatively charged membrane. In some embodiments, the capture surface is an S membrane, which is a negatively charged membrane and is a cation exchanger with sulfonic acid groups. For example, the S membrane is functionalized with sulfonic acid, $R-CH_2-SO_3^-$. In some embodiments, the capture surface is a D membrane, which is a weak basic anion exchanger with diethylamine groups, $R-CH_2-NH^+(C_2H_5)_2$. In some embodiments, the capture surface is a metal chelate membrane. For example, the membrane is an IDA membrane, functionalized with minodiacetic acid $-N(CH_2COOH^-)_2$. In some embodiments, the capture surface is a microporous membrane, functionalized with aldehyde groups, —CHO. In other embodiments, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In embodiments where the capture surface is charged, microvesicles can be isolated with a positively charged filter.

In embodiments where the capture surface is charged, the pH during microvesicle capture is a pH≤7. In some embodiments, the pH is greater than 4 and less than or equal to 8.

Depending on the membrane material, the pore sizes of the membrane range from 3 μm to 20 nm.

In some embodiments, the capture surface is a membrane. The surface charge of the capture surface can be positive, negative or neutral. In some embodiments, the capture surface is a positively charged bead or beads. For example, the bead is magnetic. Alternatively, the bead is non-magnetic. In yet another embodiment, the bead is functionalized with an affinity ligand, an antibody or a capture oligo.

The methods provided herein include a lysis reagent. In some embodiments, the agent used for on-membrane lysis is a phenol-based reagent. In some embodiments, the lysis reagent is a guanidinium-based reagent. In some embodiments, the lysis reagent is a high salt-based buffer. In some embodiments, the lysis reagent is QIAzol.

In some embodiments, the methods include one or more wash steps, for example, after contacting the biological sample with the capture surface. In some embodiments, detergents are added to the wash buffer to facilitate removing the non-specific binding (i.e., contaminants, cell debris, and circulating protein complexes or nucleic acids), to obtain a more pure microvesicle fraction. Detergents suitable for use include, but are not limited to, sodium dodecyl sulfate (SDS), Tween-20, Tween-80, Triton X-100, Nonidet P-40 (NP-40), Brij-35, Brij-58, octyl glucoside, octyl thioglucoside, CHAPS or CHAPSO.

In some embodiments, the capture surface, e.g., membrane, is housed within a device used for centrifugation; e.g. spin columns, or for vacuum system e.g. vacuum filter holders, or for filtration with pressure e.g. syringe filters. In a preferred embodiment, the capture surface is housed in a spin column or vacuum system.

The isolation of microvesicles from a biological sample prior to extraction of nucleic acids is advantageous for the following reasons: 1) extracting nucleic acids (from microvesicles provides the opportunity to selectively analyze disease or tumor-specific nucleic acids obtained by isolating disease or tumor-specific microvesicles apart from other microvesicles within the fluid sample; 2) nucleic acid-containing microvesicles produce significantly higher yields of nucleic acid species with higher integrity as compared to the yield/integrity obtained by extracting nucleic acids directly from the fluid sample without first isolating microvesicles; 3) scalability, e.g., to detect nucleic acids expressed at low levels, the sensitivity can be increased by concentrating microvesicles from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; and 5) more choices in nucleic acid extraction methods can be utilized as isolated microvesicle fractions can be of a smaller volume than that of the starting sample volume, making it possible to extract nucleic acids from these fractions or pellets using small volume column filters. The isolation of microvesicles from a biological sample prior to extraction of proteins is advantageous for the following reasons: 1) extracting proteins (from microvesicles provides the opportunity to selectively analyze disease or tissue-specific proteins obtained by isolating disease or tissue-specific microvesicles apart from other microvesicles within the fluid sample; 2) protein-containing microvesicles produce tissue-specific proteins with higher purity as compared to the yield/integrity obtained by extracting proteins directly from the fluid sample without first isolating microvesicles; 3) scalability, e.g., to detect proteins expressed at low levels, the sensitivity can be increased by concentrating microvesicles from a larger volume of sample using the methods described herein; 4) more pure or higher quality/integrity of proteins in that non-relevant proteins, lipids, cell debris, cells and other potential contaminants and inhibitors that are naturally found within biological samples are excluded before the protein extraction step; and 5) more choices in protein purification/isolation methods can be utilized as isolated microvesicle fractions can be of a smaller volume than that of the starting sample volume, making it possible to extract proteins from these fractions or pellets using small volume column filters.

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner. In some embodiments, prior to or following an isolation step of a microvesicle, the method further comprises (i) processing microvesicles to exclude lipids, cellular debris, non-relevant microvesicles from non-diseased tissue and other contaminants; (ii) purifying microvesicles using ultracentrifugation or a nanomembrane ultrafiltration concentrator; and (iii) washing the microvesicles.

In some embodiments, the sample is not pre-processed prior to isolation and extraction of nucleic acids, e.g., DNA and/or DNA and RNA, or proteins from the biological sample.

In some embodiments, the sample is subjected to a pre-processing step prior to isolation, purification or enrichment of the microvesicles is performed to remove large unwanted particles, cells and/or cell debris, non-relevant, non-disease microvesicles and other contaminants present in the biological sample. The pre-processing steps may be achieved through one or more centrifugation steps (e.g., differential centrifugation) or one or more filtration steps (e.g., ultrafiltration), or a combination thereof. The processing step may be achieved by immune-capturing specific microvesicles before or after isolation, purification of microvesicles. Where more than one centrifugation pre-processing steps are performed, the biological sample may be centrifuged first at the lower speed and then at the higher speed. If desired, further suitable centrifugation pre-processing steps may be carried out. Alternatively or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 µm filter.

In some embodiments, the sample is pre-filtered to exclude particles larger than 0.8 µm. In some embodiments, the sample includes an additive such as EDTA, sodium citrate, and/or citrate-phosphate-dextrose. In some embodiments, the sample is pre-cleared of non-relevant microvesicles or pre-enriched for relevant microvesicles.

In some embodiments, one or more centrifugation steps are performed before or after contacting the biological sample with the capture surface to separate microvesicles and concentrate the microvesicles isolated from the biological fraction. For example, the sample is centrifuged at 20,000 g for 1 hour at 4° C. To remove large unwanted particles, cells, and/or cell debris, the samples may be centrifuged at a low speed of about 100-500 g, preferably about 250-300 g. Alternatively or in addition, the samples may be centrifuged at a higher speed. Suitable centrifugation speeds are up to about 200,000 g; for example from about 2,000 g to less than about 200,000 g. Speeds of above about 15,000 g and less than about 200,000 g or above about 15,000 g and less than about 100,000 g or above about 15,000 g and less than about 50,000 g are preferred. Speeds of from about 18,000 g to about 40,000 g or about 30,000 g; and from about 18,000 g to about 25,000 g are more preferred. Particularly preferred is a centrifugation speed of about 20,000 g. Generally, suitable times for centrifugation are from about 5 minutes to about 2 hours, for example, from about 10 minutes to about 1.5 hours, or more preferably from about 15 minutes to about 1 hour. A time of about 0.5 hours may be preferred. It is sometimes preferred to subject the biological sample to centrifugation at about 20,000 g for about 0.5 hours. However the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., preferably about 1-5° C., e.g., about 3° C. or about 4° C.

In one embodiment, the method comprises a step of filtration concentration. In some embodiments, the filtration concentration step uses a filter having a molecular weight cutoff that retains the microvesicle fraction and removes all other cell fractions and cell debris. In some embodiments, the filter has a molecular weight cutoff of at least 100 kDa.

In some embodiments, one or more filtration steps are performed before or after contacting the biological sample with the capture surface. A filter having a size in the range about 0.1 to about 1.0 µm may be employed, preferably about 0.8 µm or 0.22 µm. The filtration may also be performed with successive filtrations using filters with decreasing porosity.

In some embodiments, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the microvesicles. This may consist of a series of differential centrifugations. The microvesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the microvesicle fraction. In another embodiment, the filtration is an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, G F, Sepracor). Within the scope of the invention, the use of membranes with a cut-off threshold below 1000 kDa, preferably between 100 kDa and 1000 kDa, or even more preferably between 100 kDa and 600 kDa, is advantageous.

In some embodiments, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are preferably used. For example, such supports include, but are not limited to: SUPERDEX® 200HR (Pharmacia), TSK G6000 (TosoHaas) or SEPHACRYL® S (Pharmacia).

In some embodiments, one or more affinity chromatography steps are performed before or after contacting the biological sample with the capture surface. Some microvesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of long, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

Optionally, control particles may be added to the sample prior to microvesicle isolation or nucleic acid (or protein) extraction to serve as an internal control to evaluate the efficiency or quality of microvesicle purification and/or nucleic acid extraction. The methods described herein provide for the efficient isolation and the control particles along with the microvesicle fraction. These control particles include Q-beta bacteriophage, virus particles, or any other particle that contains control nucleic acids (e.g., at least one control target gene) that may be naturally occurring or engineered by recombinant DNA techniques. In some embodiments, the quantity of control particles is known before the addition to the sample. The control target gene can be quantified using real-time PCR analysis. In some embodiments, the size of control particles is known before the addition to the sample. Quantification of a control target gene can be used to determine the efficiency or quality of the microvesicle purification or nucleic acid extraction processes.

Preferably, the control particle is a Q-beta bacteriophage, referred to herein as "Q-beta particle." The Q-beta particle used in the methods described herein may be a naturally-occurring virus particle or may be a recombinant or engineered virus, in which at least one component of the virus particle (e.g., a portion of the genome or coat protein) is synthesized by recombinant DNA or molecular biology techniques known in the art. Q-beta is a member of the laviviridae family, characterized by a linear, single-stranded RNA genome that consists of 3 genes encoding four viral proteins: a coat protein, a maturation protein, a lysis protein, and RNA replicase. Due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. After addition of the Q-beta particles to the biological sample, the nucleic acids from the Q-beta particle are extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added can be compared to determine the quality of the isolation and/or extraction process.

In a preferred embodiment, the Q-beta particles are added to the urine sample prior to nucleic extraction. For example, the Q-beta particles are added to the urine sample prior to ultrafiltration and/or after the pre-filtration step.

In some embodiments, 50, 100, 150, 200, 250, 300, 350, 400, 450, 500, 1,000 or 5,000 copies of Q-beta particles added to a bodily fluid sample. In a preferred embodiment, 100 copies of Q-beta particles are added to a bodily fluid sample. The copy number of Q-beta particles can be calculated based on the ability of the Q-beta bacteriophage to infect target cells. Thus, the copy number of Q-beta particles is correlated to the colony forming units of the Q-beta bacteriophage.

In some embodiments, the methods and kits described herein include one or more in-process controls. In some embodiments, the in-process control is detection and analysis of a reference gene that indicates sample quality (i.e., an indicator of the quality of the body fluid sample). In some embodiments, the reference gene(s) is/are a sample-inherent transcript. In some embodiments, the reference gene(s) is/are analyzed by additional qPCR.

In some embodiments, the extracted nucleic acids or proteins are subject to further analysis. Various nucleic acid sequencing and protein identification techniques are used to detect and analyze nucleic acids (such as cell free DNA and/or RNA) or proteins extracted from the microvesicle fraction from biological samples. Analysis of nucleic acids or proteins extracted from microvesicles for diagnostic purposes has wide-ranging implications due to the non-invasive nature in which microvesicles can be easily collected.

Detection of Nucleic Acid Biomarkers

In some embodiments, the extracted nucleic acid comprises DNA and/or DNA and RNA. In embodiments where the extracted nucleic acid comprises DNA and RNA, the RNA is preferably reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR or RNA sequencing. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample).

In another embodiment, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

Hence, in some embodiments, a methods of determining, assessing, measuring, characterizing or assaying gene expression, is carried out using RT-PCR. In other embodiments, the method of determining, assessing, measuring, characterizing or assaying gene expression, is performed according to any other PCR method known in the art for measuring gene expression.

In some embodiments, the methods of comparing nucleic acids extracted from a sample to a control set of genes or to a gene signature as further provided herein, comprises using RT-PCR, quantitative PCR (qPCR) or any other methodology known in the art to be useful for comparing gene expression of at least one or more genes.

In some embodiments, one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated microvesicles, whether wild type or variants, are identified with methods known in the art.

The present invention also includes various uses of the new methods of isolating microvesicles from a biological sample for high quality nucleic acid extraction from a biological sample for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

Detection of Exosome Protein Biomarkers

Extracellular vehicles (EVs) isolated from body fluids using the methods described herein contain many types of protein that are associated with diseases or medical conditions, and these protein biomarkers are important for the diagnosis, and monitoring of medical conditions.

Herein are described protein biomarkers extracted from urine extracellular vehicles (EVs) and used for assessing and/or monitoring kidney transplant rejection. While the examples provided herein use a variety of membranes and devices used for centrifugation and/or housing device that allows for the efficient capture of EVs and release of the proteins contained therein.

Methods of protein detection from microvesicles isolations can be any method used in the art. The protein may be proteins on the surface of the EV, or contained within the EV.

In some embodiments, the EV protein analysis uses methods to identify proteins on the surface of intact microvesicles. Intact exosomes may be isolated using a variety of methods of eluting intact exosomes from the capture surface. For example, some methods use size exclusion chromatography. In other embodiments, intact vesicles are eluted off a capture material using elution buffers. Elution buffers can be buffers possessing a pH of 3 up to a pH of 8.5. In other embodiments, intact EVs may be isolated from urine or plasma using filtration membranes. In other embodiments, the microvesicles can be eluted from affinity capture materials by linker molecules that separate and release the microvesicle when exposed to light, UV light, pH changes or enzymes.

In other embodiments, protein detection assays from the art will be used to examine EV proteins that are lysed from EVs. Intact EVs may be extracted away from the capture material and then lysed. In some embodiments, the EVs proteins are extracted from the capture surface by adding lysis buffer directly to the surface. Protein purification methods are used to identify proteins on intact EV, lysed EVs or a combination thereof.

Methods of protein detection from the art that identify proteins may be quantitative or qualitative. Some methods detect native proteins; some detect denatured proteins, some detect protein complexes, some detect protein aggregates, polypeptides, lipoproteins and/or protein modifications. When intact vesicle proteins are used, it may be preferred, but not required, to use a method that detects proteins in native conformation. In some embodiments when lysed proteins from EVs are used, it is often, although not required that methods to detect denatured proteins are used.

In other embodiments, the detection and/or quantitation of intact and/or lysed proteins present in the extracellular vesicles isolated from body fluids can be carried out/measured using any of a variety of art-recognized techniques including, but not limited to enzyme-linked immunosorbent assay (ELISA), western immunoblotting, proximity ligation assay (PLA), proximity extension assay (PEA), immunofluorescence assay (IF), immunohistochemistry (IHC), Immunocytochemistry (ICC), Flow cytometry and FACS analysis, Immunoprecipitation (IP), Enzyme linked immunospot (ELISPOT), Meso Scale Discovery ELISA assay, aptamer-based assays, Surface Plasmon Resonance, Raman spectroscopy, enzymatic assays, Fluorescence Resonance Energy Transfer (FRET), Homogeneous Time Resolved Fluorescence (HTFR), mass spectrometry and/or total protein concentration assays such as Bradford protein assay, or the bicinchoninic acid assay (BCA assay), also known as the Smith assay. In some embodiments, a combination of the methods described herein were used.

In some embodiments, antibodies-based detection methods are used. In other methods, aptamer or synthetic antibody detection methods are used.

Kits for Isolating Microvesicles from a Biological Sample

One aspect of the present invention is further directed to kits for use in the methods disclosed herein. The kit comprises a capture surface apparatus sufficient to separate microvesicles from a biological sample from unwanted particles, debris, and small molecules that are also present in the biological sample. The present invention also optionally includes instructions for using the foregoing reagents in the isolation and optional subsequent nucleic acid and/or protein extraction process.

EXAMPLES

While the examples provided herein use a variety of membranes and devices used for centrifugation and/or filtration purposes, it is to be understood that these methods can be used with any capture surface and/or housing device that allows for the efficient capture of microvesicles and release of the nucleic acids, particularly, RNA, contained therein.

Example 1: Discovery and Validation of a Urinary Exosome mRNA Signature for the Diagnosis of Kidney Transplant Rejection In the studies presented herein, urine samples were collected from patients undergoing a transplant kidney biopsy for clinical indications. RNA from the urinary exosomes were isolated from up to 20 mL urine for expression profiling. Two patient cohorts were screened, first to generate a candidate maker panel (training) and a second to verify the performance of the smaller panel (validation). RNA from the exosomes, also referred herein as exoRNA, was reverse transcribed and pre-amplified prior to analysis of RNA signature using the OpenArray™ Human Inflammation Panel. OpenArray is a TaqMan qPCR array. Human Inflammation Panel consists of 586 targets and 21 endogenous control assays. Rejection criteria for urine samples from kidney transplant rejection patients includes cellular rejection including borderline rejection, antibody mediated rejection (AMR) either acute or chronic active or cellular and AMR. No rejection urine sample from kidney transplant patients have no symptoms, no clinical indications of either cellular or antibody-mediated transplant rejection. In addition, three in-house urine control samples were used: one pooled human male and female sample (CTRL_1), one pooled human male sample (CTRL_M), and one pooled human female sample (CTRL_F).

A brief description of each subject is provided below in Table 1 and Table 2:

TABLE 1

Training Cohort Patient Information. Each patient was characterized by rejection status and the nature of the rejection (AMR - antibody-mediated rejection, * -samples rejected during RNA extraction)

| Patient ID | Status | Rejection Type |
| --- | --- | --- |
| EX01-01a | Rejection | Cellular |
| EX01-01b* | Rejection | Cellular |
| EX01-02a | Non-rejection | |
| EX01-02b | Non-rejection | |
| EX01-04 | Rejection | AMR, chronic |
| EX01-08a | Non-rejection | |
| EX01-08b | Non-rejection | |
| EX01-10 | Rejection | Acute cellular IB |
| EX01-17 | Rejection | Acute cellular IA |
| EX01-18 | Rejection | Acute cellular IB |
| EX01-19a | Non-rejection | |
| EX01-19b | Non-rejection | |
| EX01-20* | Non-rejection | |
| EX01-26 | Non-rejection | |
| EX01-27 | Rejection | Acute cellular IA |
| EX01-28 | Non-rejection | |
| EX01-29 | Rejection | AMR, chronic |
| EX01-31 | Rejection | AMR, mild |
| EX01-32 | Rejection | AMR, chronic |
| EX01-33 | Non-rejection | |
| EX01-35 | Rejection | Acute cellular, mild, plasma rich |
| EX01-37 | Non-rejection | |
| EX01-38 | Non-rejection | |
| EX01-39 | Rejection | Acute cellular, mild/AIN |
| EX01-40 | Non-rejection | |
| EX01-46 | Rejection | Acute cellular/AMR |
| EX01-50 | Non-rejection | |
| EX01-51 | Rejection | AMR, acute |

TABLE 2

Validation Cohort Patient Information. Each patient was characterized by rejection status and the nature of the rejection (AMR - antibody-mediated rejection, * - samples rejected during RNA extraction, † - pre-rejection samples)

| Patient ID | Status | Rejection cause |
| --- | --- | --- |
| EX01-05 | Non-rejection | |
| EX01-09 | Non-rejection | |
| EX01-11 | Non-rejection | |
| EX01-13 | Rejection | Borderline cellular |
| EX01-20 | Non-rejection | |
| EX01-21 | Rejection | Cellular/AMR, chronic |
| EX01-22* | Non-rejection | |
| EX01-27a | Rejection | Acute cellular, chronic |
| EX01-27b | Rejection | Acute cellular, chronic |
| EX01-29a† | Rejection | Borderline cellular/AMR, chronic |
| EX01-29b | Rejection | Borderline cellular/AMR, chronic |
| EX01-29c | Rejection | Borderline cellular/AMR, chronic |
| EX01-36 | Rejection | Cellular, plasma rich |
| EX01-37 | Rejection | Borderline cellular |
| EX01-39 | Rejection | Acute cellular, early/mild |
| EX01-43 | Rejection | AMR, chronic |
| EX01-46 | Rejection | AMR, chronic |
| EX01-47 | Non-rejection | |
| EX01-51 | Rejection | Borderline cellular |
| EX01-52a† | Rejection | Cellular, early/mild |
| EX01-52b | Rejection | Cellular, early/mild |
| EX01-54 | Rejection | AMR, acute |
| EX01-55 | Non-rejection | |
| EX01-56a | Rejection | AMR, acute |
| EX01-56b | Rejection | AMR, acute |
| EX01-57a† | Rejection | Acute cellular, chronic |
| EX01-57b | Rejection | Acute cellular, chronic |

TABLE 2-continued

Validation Cohort Patient Information. Each patient was characterized by rejection status and the nature of the rejection (AMR - antibody-mediated rejection, * - samples rejected during RNA extraction, † - pre-rejection samples)

| Patient ID | Status | Rejection cause |
|---|---|---|
| EX01-57c | Rejection | Acute cellular, chronic |
| EX01-59 | Non-rejection | |
| EX01-60 | Rejection | Cellular |
| EX01-61 | Non-rejection | |
| EX01-64 | Rejection | Acute cellular, early/mild |
| EX01-65 | Non-rejection | |
| EX01-67 | Rejection | Cellular |
| EX01-68 | Rejection | Cellular/AMR chronic |
| EX01-70 | Non-rejection | |
| EX01-74 | Non-rejection | |
| EX01-77 | Non-rejection | |

Figure 2:
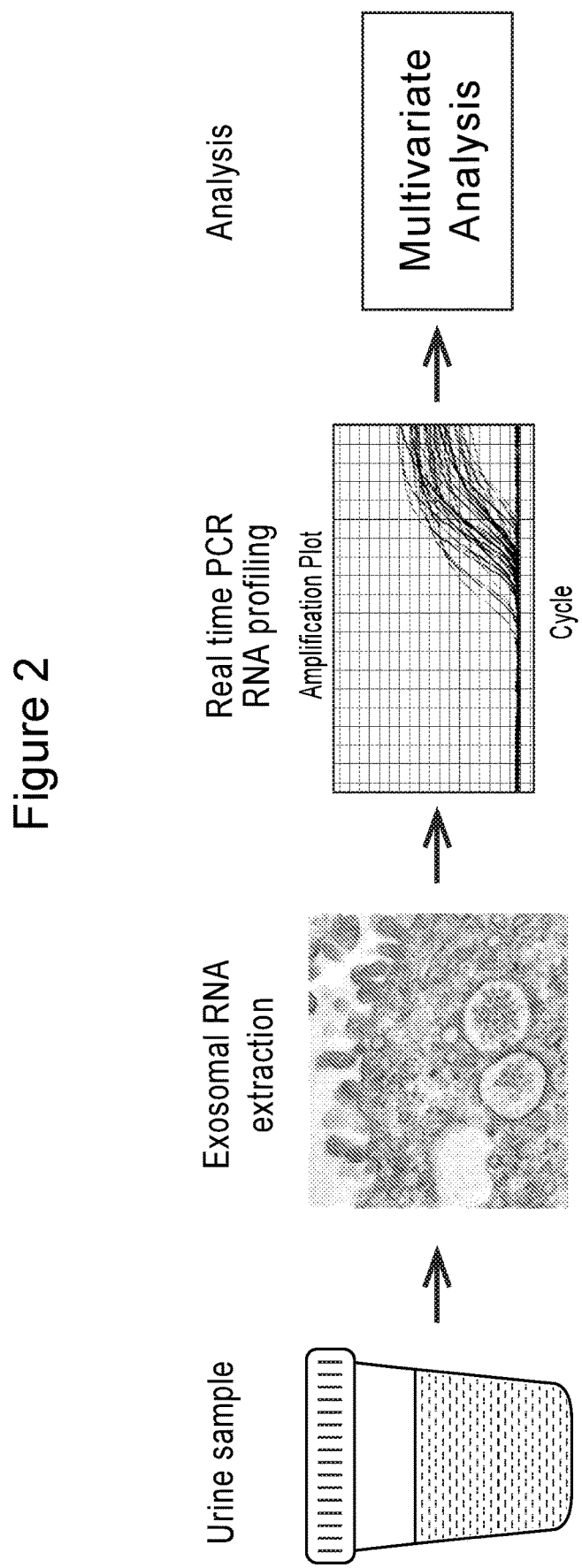
FIG. 2 illustrates urine samples that are collected and stored until processing. Exosomal RNA is extracted using clinical sample concentrator filter membrane. Exosomal RNA is extracted from concentrated microvesicles and analyzed for expression of transcripts related to inflammation by real time PCR.

Briefly, the study design was as follows: 20 mL urine sample was centrifuged 2000×g for 20 minutes. The supernatant was then processed to extract EV RNA using urine clinical sample concentration (uCSC) as described in PCT Application Publication Nos. WO 2014/10757, WO2015/021158, WO2016/007755 and WO2016/054252. The pellet was then processed to extract RNA. RNA was eluted in nuclease-free water and reverse transcribed using VILO cDNA synthesis kit according to manufacturer's instructions. RNA profiling was performed, (FIG. 2).

The OpenArray (OA) Human Inflammation Panel was run through TaqMan qPCR assays. In total 586 target assays were run on genes that have been studied as target for a range of inflammatory diseases, along with 21 endogenous control assays.

Figure 3A:
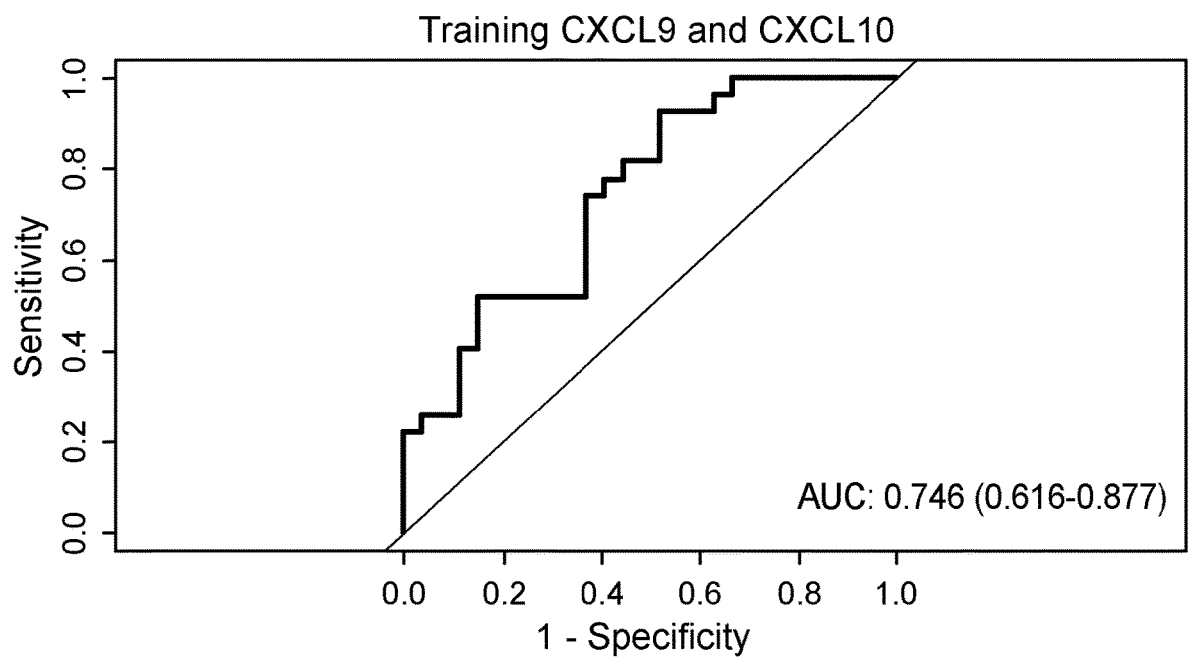
FIG. 3 illustrates a receiver-Operating-Characteristic (ROC) curve for Diagnosis kidney Rejection using exoRNA CXCL9 and CXCL10 as biomarkers for the training (FIG. 3A) and validation (FIG. 3B) sets with IL17RA as the normalizer.
Figure 3B:
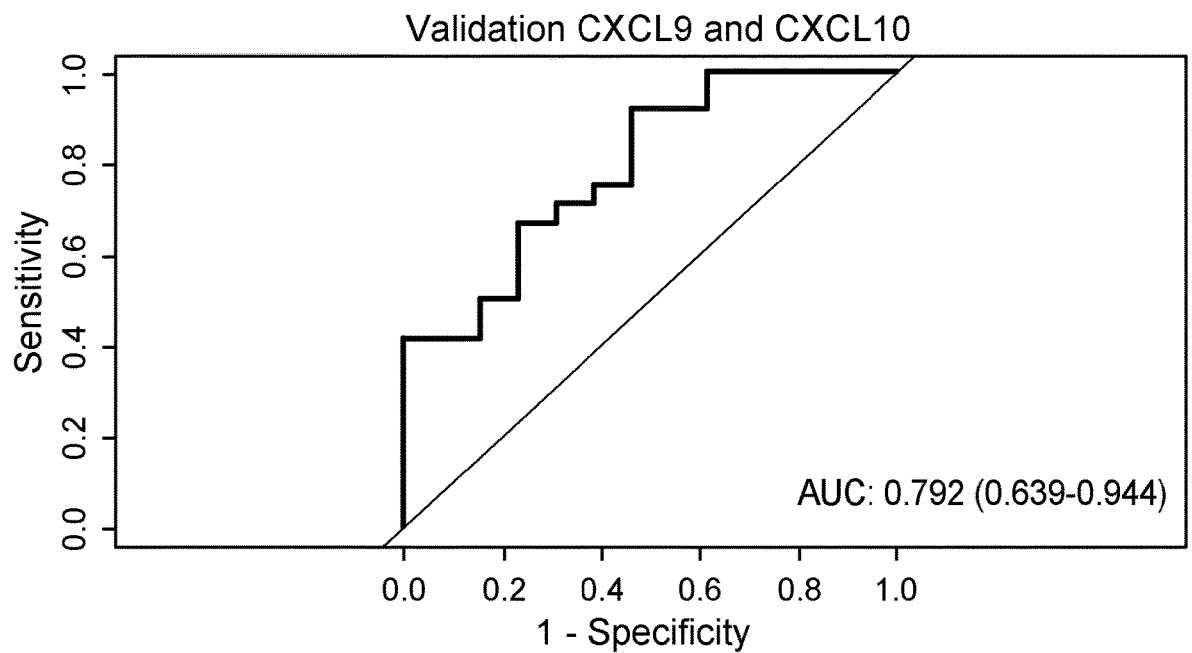

The raw data from the 607 assays for each sample is then subjected to statistical analysis, overall clustering to reveal signatures for rejection and non-rejection and multivariate logistic regression analysis. Statistical analysis determined a three-gene signature derived from EVs in a urine sample was significantly capable of differentiating patients who experienced kidney transplant rejection from those patients who did not exhibit indications of rejection. The signature included genes CXCL9, CXCL10 and IL17RA. The performance of the 3-gene signature was evaluated by multivariate-logistic regression and is shown in FIGS. 3A and 3B. The Receiver-operator-characteristic (ROC) analysis of the signature demonstrated a significant area under the curve (AUC) of 0.792, FIG. 3B.

Thus, the studies presented herein have identified a 3-gene signature in urine exosomes that is useful in assessing patients with kidney transplant rejection.

Example 2: Discovery of Urinary Exosome Proteins for the Diagnosis of Kidney Transplant Rejection In the studies presented herein, urine samples were collected from patients undergoing a transplant kidney biopsy for clinical indications. Nine kidney transplant subjects with no clinical or sub-clinical indications of rejection were used along with 10 kidney transplant subjects with cellular, or antibody mediated or clinical rejection, see Table 3, patient information.

TABLE 3

Patient Information. Protein Cohort Patient Information. Each patient was characterized by rejection status and the nature of the rejection (AMR - antibody-mediated rejection)

| Patient ID | Status | Rejection Type |
|---|---|---|
| EX01-01a | Rejection | Cellular |
| EX01-02b | Non-rejection | |
| EX01-08a | Non-rejection | |
| EX01-17 | Rejection | Acute cellular IA |
| EX01-18 | Rejection | Acute cellular IB |
| EX01-19a | Non-rejection | |
| EX01-26 | Non-rejection | |
| EX01-29 | Rejection | AMR, chronic |
| EX01-31 | Rejection | AMR, mild |
| EX01-32 | Rejection | AMR, chronic |
| EX01-33 | Non-rejection | |
| EX01-35 | Rejection | Acute cellular, mild, plasma rich |
| EX01-38 | Non-rejection | |
| EX01-39 | Rejection | Acute cellular, mild/AIN |
| EX01-46 | Rejection | Acute cellular/AMR |
| EX01-50 | Non-rejection | |
| EX01-51 | Rejection | AMR, acute |

Protein from the urinary exosomes were isolated from up to 10 mL urine for expression profiling. Urine exosomes were isolated using an exosome capture affinity membrane. In short, 10 mL of patient or control urine was added to the exosome capture membrane column until the entire sample was passed through the column. The column was then washed with 15 mL of wash buffer and intact exosomes were eluted with 400 μL elution buffer. In one embodiment, the EV elute for each sample was assayed for inflammatory proteins using proximity extension assay (PEA). A proteomic assay array targeting 92 inflammatory proteins was run on each urinary exosome eluate using the Proseek™ Multiplex Inflammation Panel (OLINK Proteomics, Uppsala, Sweden). In another embodiment, inflammatory proteins were quantitated from each urine-derived EV sample using ELISA and/or western blot, and/or other protein detection methods. Urinary extracellular vesicle associated proteins were identified here in and listed in Table 4.

TABLE 4

Proteins detected in urine EVs that can be used as biomarkers. Proteins detected in urinary EVs that may be used as a biomarker for transplant rejection

| | | | | |
|---|---|---|---|---|
| IL-8 | MCP-4 | 4E-BP1 | CXCL1 | TNF |
| VEGF-A | CCL11 | IL-20 | TSLP | CCL23 |
| MCP-3 | TNFSF14 | SIRT2 | CCL4 | CD5 |
| CDCP1 | FGF-23 | CCL28 | CD6 | MIP-1 alpha |
| CD244 | FGF-5 | DNER | SCF | Flt3L |
| IL-7 | MMP-1 | EN-RAGE | IL-18 | CXCL6 |
| OPG | LIF-R | CD40 | TGFA | CXCL10 |
| LAP TGF-beta-1 | FGF-21 | FGF-19 | IL-12B | ST1A1 |
| uPA | CCL19 | LIF | IL-24 | STAMPB |
| IL-6 | IL-15RA | MCP-2 | ARTN | ADA |
| IL-17C | IL-10RB | CASP-8 | MMP-10 | TNFB |
| MCP-1 | IL-18R1 | CCL25 | IL-10 | CSF-1 |

TABLE 4-continued

Proteins detected in urine EVs that can be used as biomarkers.
Proteins detected in urinary EVs that may
be used as a biomarker for transplant rejection

| IL-17A | PD-L1 | CX3CL1 | CXCL9 | IL-20RA |
| CXCL11 | Beta-NGF | TNFRSF9 | CST5 | HGF |
| AXIN1 | CXCL5 | NT-3 | IL-2RB | CCL20 |
| TRAIL | TRANCE | TWEAK | IL-1 alpha | OSM |

Figure 4:
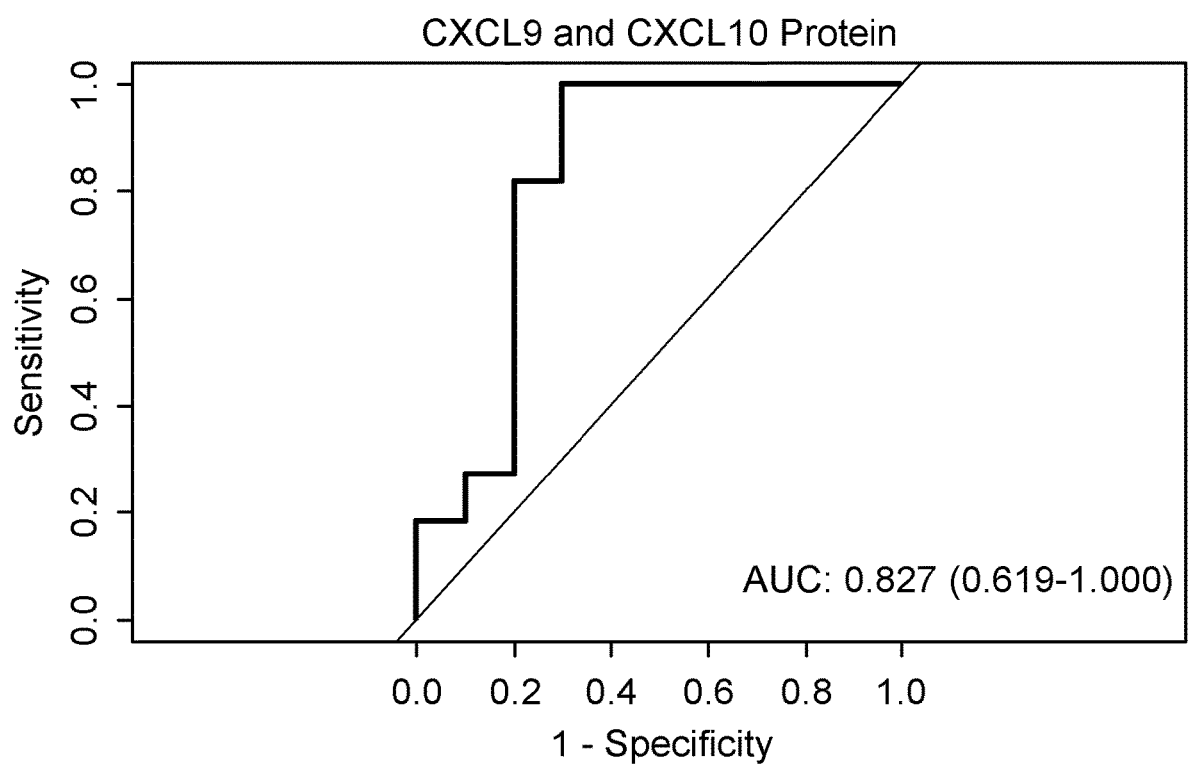
FIG. 4 illustrates a receiver-operating-characteristic (ROC) curve for Diagnosis of Acute Rejection using protein expression of CXCL9 and CXCL10 as biomarkers. Fraction of true positive results (sensitivity) and the fraction of false positive results (1−specificity) for diagnosis of acute rejection using CXCL9 and CXCL10.

In addition to the EV mRNA CXCL9 and CXCL10 gene expression data, CXCL9 and CXCL10 protein expression values were also significantly capable of differentiating between rejection and non-rejection urinary exosome samples (FIG. 4), further validating the exoRNA signature described herein. Multivariate logistic regression showed the diagnostic performance of CXCL9 and CXCL10 protein was highly significant (Receiver-Operator-Characteristic (ROC) AUC=0.827), (FIG. 4).

Figure 5:
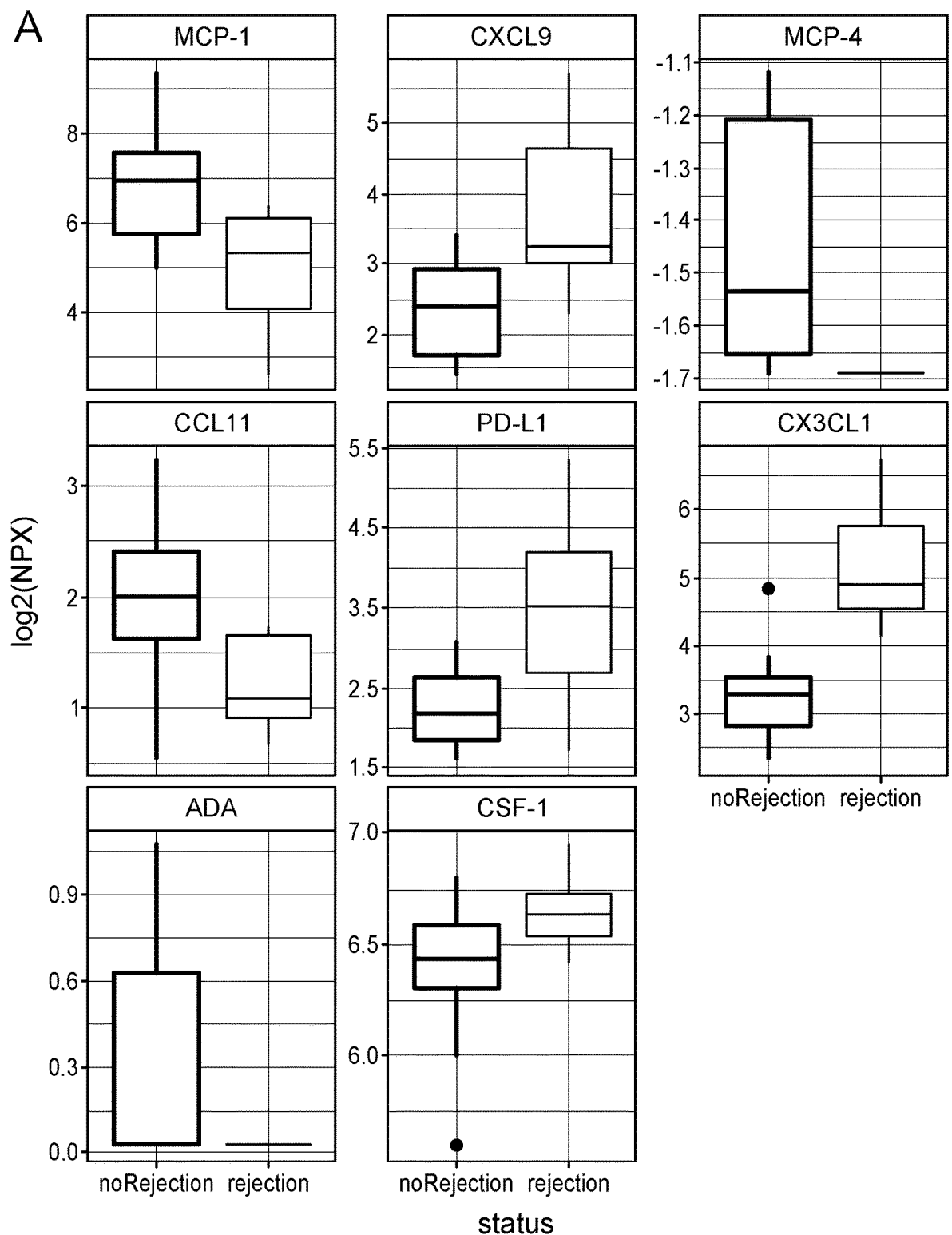
FIG. 5 illustrates that urine exosome proteins are differentially expressed and capable of identifying samples with kidney rejection from non-rejection.
Figure 6:
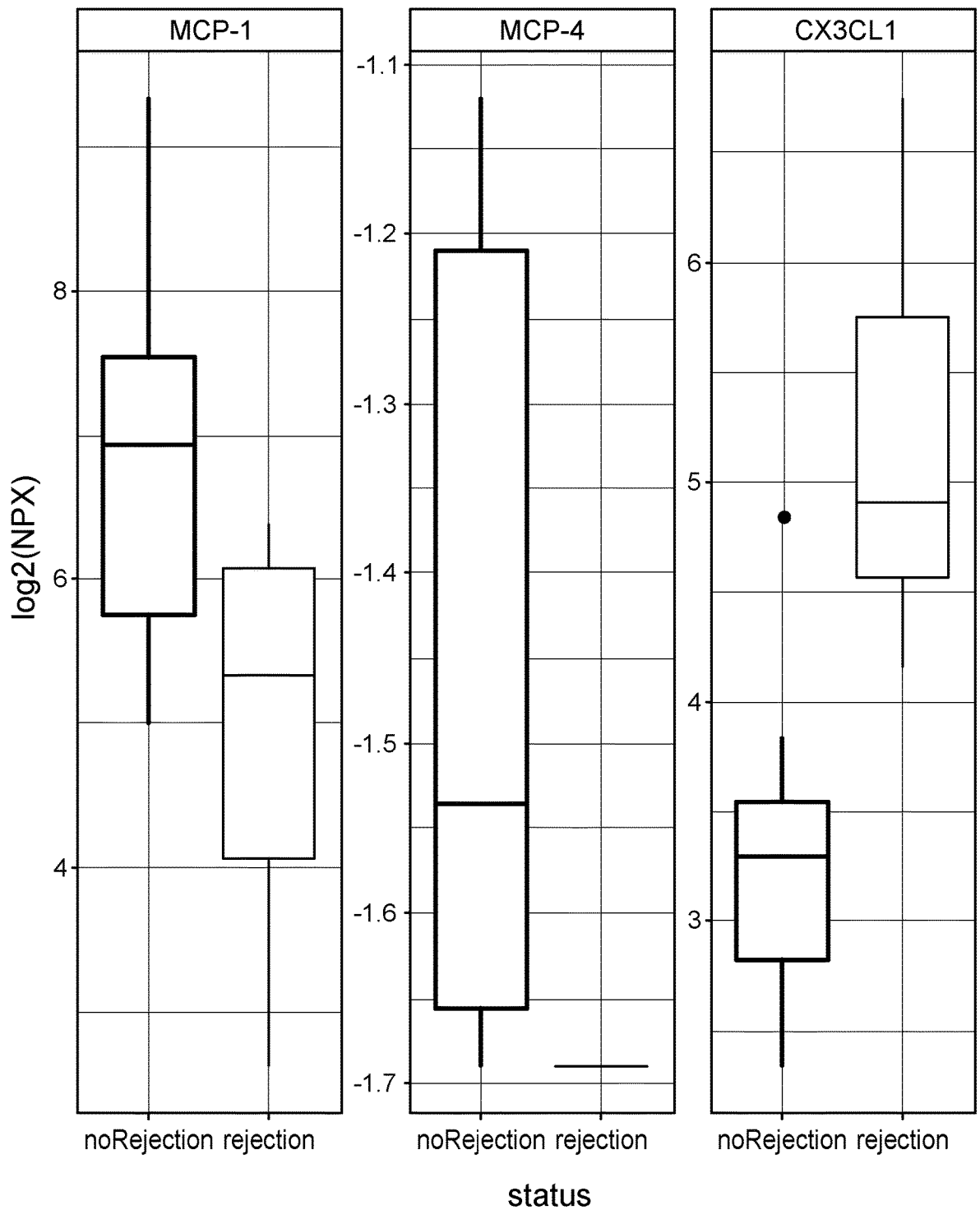
FIG. 6 illustrates that urine exosome proteins MCP-1, MCP-4 and CX3CL1 accurately identify individuals with kidney rejection from those without.

The normalized protein expression data for each of the 92 protein targets in each of the 18 urine exosome sample were analyzed by ANOVA with Bonferroni correction. Of the 92 proteins examined eight were differentially expressed between rejection and non-rejection samples, MCP-4, MCP-1, CX3CL1, CXCL9, CCL11, PD-L1, ADA, CSF-1 (P=0.05), (FIG. 5). Three proteins were highly significantly different in protein expression levels between rejection and non-rejection exosome protein samples including MCP-1, MCP-4 and CX3CL1 (P=0.01), (FIG. 6).

Thus, the studies presented herein have identified a urinary EV protein profile that is highly capable of correctly assessing patients with kidney transplant rejection.

Thus, the studies presented herein have identified a gene signature and protein biomarkers in urine exosomes that is useful in assessing patients with kidney rejection. Analysis of cellular RNA from urine was unable to generate such a signature (US patent WO2017/192945 A1).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method of treating a kidney transplant rejection in a patient, the method comprising the steps of:
    a) isolating a microvesicle fraction from a urine sample from the patient;
    b) extracting nucleic acids from the microvesicle fraction;
    c) determining the expression levels of at least two biomarkers from the extracted nucleic acids, wherein the at least two biomarkers comprise each of CXCL9 and CXCL10, and the expression level of at least one normalizing gene, wherein the at least one normalizing gene comprises IL17RA;
    d) normalizing the expression levels of the at least two biomarkers to the expression level of the at least one normalizing gene;
    e) determining that the patient is undergoing a kidney transplant rejection based on the normalized expression levels of the at least two biomarkers; and
    f) administering at least one kidney transplant rejection therapy to the patient undergoing a kidney transplant rejection.

2. The method of claim 1, wherein the at least two biomarkers and the at least one normalizing gene comprise RNA.

3. The method of claim 1, wherein isolating a microvesicle fraction comprises (i) processing the microvesicle fraction to exclude lipids, cellular debris, non-relevant microvesicles and other contaminants; (ii) purifying microvesicles from the microvesicle fraction using affinity chromatography, capture column, immune-capture, ultracentrifugation or a nanomembrane ultrafiltration concentrator; and (iii) washing the microvesicles.

4. The method of claim 1, wherein said patient is undergoing a therapy for a kidney disease.

5. The method of claim 1, wherein the type of kidney transplant rejection is cellular rejection, borderline rejection, acute antibody-mediated rejection (AMR), chronic active AMR, cellular and antibody-mediated rejection, or a combination thereof.

6. The method of claim 1, wherein determining that the patient is undergoing a kidney transplant rejection based on the normalized expression levels of the at least two biomarkers comprises using an algorithm.

7. The method of claim 6, wherein said algorithm incorporates information relating to at least one of the following kidney transplant rejection risk factors:
    a) female;
    b) age <50;
    c) African American;
    d) repeat transplant;
    e) current Panel Reactive Antibody (PRA) >25%;
    f) 3-6 human leukocyte antigen (HLA) mismatches (A, B and DR)
    g) deceased donor kidney;
    h) delayed graft function;
    i) presence of donor specific antibodies;
    j) no thymoglobulin induction; or a combination thereof.

8. The method of claim 1, wherein the at least one kidney transplant rejection therapy comprises immunosuppressive therapy.

* * * * *